United States Patent [19]

Ohya et al.

[11] Patent Number: 5,071,739

[45] Date of Patent: Dec. 10, 1991

[54] SILVER HALIDE COLOR PHOTOGRAPHIC LIGHT-SENSITIVE MATERIAL CONTAINING MAGENTA COUPLER

[75] Inventors: Hidenobu Ohya; Shuji Kida, both of Tokyo, Japan

[73] Assignee: Konica Corporation, Tokyo, Japan

[21] Appl. No.: 593,042

[22] Filed: Oct. 5, 1990

[30] Foreign Application Priority Data

Oct. 9, 1989 [JP] Japan .................................. 1-263641

[51] Int. Cl.$^5$ ................................................ G03C 7/38
[52] U.S. Cl. ...................................... 430/558; 430/387
[58] Field of Search ........................ 430/558, 386, 387

[56] References Cited

U.S. PATENT DOCUMENTS

| | | | |
|---|---|---|---|
| 3,725,067 | 4/1973 | Bailey et al. ........................ | 430/558 |
| 3,758,309 | 9/1973 | Bailey et al. ........................ | 430/558 |
| 3,810,761 | 5/1974 | Bailey ................................. | 430/558 |
| 4,791,052 | 12/1988 | Kida et al. .......................... | 430/558 |
| 4,835,094 | 5/1989 | Wolff et al. ......................... | 430/558 |

FOREIGN PATENT DOCUMENTS 0284240 9/1988 European Pat. Off. .
3633364 4/1988 Fed. Rep. of Germany .

*Primary Examiner*—Charles L. Bowers, Jr.
*Assistant Examiner*—Lee C. Wright
*Attorney, Agent, or Firm*—Finnegan, Henderson, Farabow, Garrett and Dunner

[57] ABSTRACT

A silver halide color photographic light-sensitive material containing novel pyrazolotriazole type magenta couler is disclosed. The coupler is represented by the following Formula I:

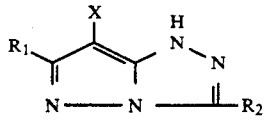

wherein $R_1$ is a primary-alkyl, a secondary-alkyl group or a tertiary-alkyl group; $R_2$ is an aralkyl group represented by the following Formula II; and X is a substituent capable of splitting off upon reaction with the oxidation product of a color developing agent;

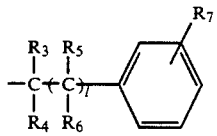

whrein $R_3$, $R_4$, $R_5$ and $R_6$, are each a hydrogen atom or an alkyl group, provided that at least one of $R_3$ and $R_4$ is an alkyl group when $R_1$ is a primary alkyl group; $R_7$ is a group having a —COOM group, in which M is a hydrogen atom or a cation; and l is 0 or 1. The light-sensitive material is excellent in color forming efficiency and color reproducibility.

8 Claims, No Drawings

SILVER HALIDE COLOR PHOTOGRAPHIC LIGHT-SENSITIVE MATERIAL CONTAINING MAGENTA COUPLER

FIELD OF THE INVENTION

This invention relates to a silver halide photographic light-sensitive material containing a magenta coupler and, particularly, to a silver halide photographic light-sensitive material in which a dye image excellent in color reproducibility and color developability can be obtained by containing a novel pyrazolotriazole type magenta coupler therein.

BACKGROUND OF THE INVENTION

In silver halide color photographic light-sensitive materials, the well-known couplers generally applicable thereto include, for example, yellow couplers of open-chained ketomethylene type compounds, magenta couplers of pyrazolone type compounds or pyrazoloazole type compounds, and cyan couplers of phenol type compounds or naphthol type compounds.

The pyrazolone type compounds have so far been used as magenta couplers. However, the dyes produced of the pyrazolone type magenta couplers have an undesirable secondary absorption which has been required to be improved.

For solving this problem, U.S. Pat. Nos. 3,725,065, 3,810,761, 3,758,309 and 3,725,067 propose the pyrazolotriazole type couplers. However, these types of pyrazolotriazole couplers having reduced secondary absorption are still not sufficient in color forming ability. Therefore, further researches and studies have been made continuously with the purpose of improving the color forming ability, such as disclosed in, for example, Japanese Patent Publication Open to Public Inspection (hereinafter referred to as Japanese Patent O.P.I. Publication) Nos. 60-55343/1985, 60-98434/1985 and 61-120152/1986.

However, most of the pyrazolotriazole type couplers described in the above-given prior art have been proved to be varied in tone according to the densities of a color developed image (hereinafter simply called a color density) when the couplers are used in silver halide photographic light-sensitive materials.

To be more concrete, it has been proved that a color reproducibility is lowered when a color density is increased, because the density on the short wavelength side is increased more than the maximum absorption density, that is, because the short wavelength side projects out on a spectral map.

The pyrazolotriazole type couplers having been researched so far include those not having the above-described problem, that is, those not having any tone difference caused by density variations. Such couplers are described in, for example, Japanese Patent O.P.I. Publication Nos. 61-120146/1986 and 61-120147/1986. However, in any one of the pyrazolotriazole type couplers which makes improvements on the above-mentioned tone difference problem caused by density variations, the color developability thereof are still unsatisfactory. It has, therefore, been desired to make the research and development of pyrazolotriazole type couplers having been made improvements on both of the tone differences caused by density variations and the color developability.

OBJECTS OF THE INVENTION

It is an object of the invention to provide a silver halide color photographic light-sensitive material in which the pyrazolotriazole type couplers thereof can be excellent in both color developability and color reproducibility and made improvements on tone difference caused by density variations.

Another object of the invention is to provide a silver halide color photographic light-sensitive material in which the pyrazolotriazole type couplers thereof having a limited color developability variation against the pH variations of the processing solutions therefor.

SUMMARY OF THE INVENTION

The objects of the invention can be achieved with a silver halide photographic light-sensitive material comprising a support having thereon a silver halide emulsion layer containing a magenta coupler represented by the following Formula I:

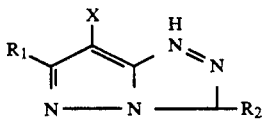

wherein $R_1$ is a primary-alkyl group, a secondary-alkyl group or a tertiary alkyl group; Rhd 2 is an aralkyl group represented by the following Formula II; X is a substituent capable of splitting-off upon reaction with the oxdation product of a color developing agent;

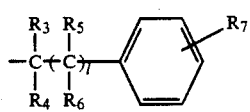

Formula II wherein Rhd 3, Rhd 4, Rhd 5 and Rhd 6, are each a hydrogen atom or an alkyl group, provided that at least one of Rhd 3 and Rhd 4 is an alkyl group when $R_1$ is a primary-alkyl group; Rhd 7 is a group having a —COOM group, in which M is a hydrogen atom or a cation; and l is 0 or 1.

DETAILED DESCRIPTION OF THE INVENTION

About the pyrazolotriazole type couplers represented by Formula I, which are applicable to the invention, will be detailed.

In Formula I, $R_1$ represents any one of alkyl groups including, for example; primary alkyl groups such as a methyl group, an ethyl group, a propyl group, a butyl group, a pentyl group, a hexyl group, a decyl group, a pentadecyl group, a hexadecyl group, a heptadecyl group, and an octadecyl group; and secondary or tertiary alkyl groups such as an isopropyl group, a sec-butyl group, a 2-methyl-butyl group, a 2-hexylnonyl group, a t-butyl group, a t-pentyl group, a 2,2-dimethyl-butyl group, a 2,2-dipentyl-nonyl group; provided, the primary, secondary and tertiary alkyl groups each may further have substituents including, for example; halogen atoms such as fluorine atom and chlorine atom, alkyl groups such as a methyl group, an ethyl group, a propyl group, an n-butyl group, a t-butyl group, an n-pentyl group, a t-amyl group, an n-hexyl group, an n-heptyl group, an n-octyl group, and an n-decyl group, alkenyl groups such as a vinyl group, alkinyl groups such as a 1-propenyl group, aryl groups such as a phenyl group, a 4-t-butylphenyl group, and a 2,4-di-t-amylphenyl group heterocyclic groups such as a 2-furyl group, and a thienyl group, cyano groups, hydroxy groups, alkoxy groups such as a methoxy group, an ethoxy group, a 2-methanesulfonylethoxy group, and an n-butoxy group, aryloxy groups such as a phenoxy group, a 2,4-di-t-acylphenoxy group, acyloxy groups such as an acetoxy group, and a hexadecanoyloxy group, acylamino groups such as an acetoamido group, a benzamido group, and an α-(2,4-di-t-acylphenoxy)-butylamido group, anilino groups such as a phenylamino group, amino groups such as an ethylamino group, and a dimethylamino group, sulfonyl groups such as a methanesulfonyl group, and a hexadecanesulfonyl group, acyl groups such as an acetYl group, and a benzoyl group, alkoxycarbonyl groups such as a methoxycarbonyl group, and an ethoxycarbonyl group.

The alkyl groups preferably used as $R_1$ include, for example, a methyl group, an i-propyl group, and a t-butyl group.

Next, X denoted in Formula I will be detailed.

X represents a group releasable from the structure of Formula I upon coupling reaction with the oxidized products of a color developing agent. Such groups include, for example, a halogen atom, an alkoxy group, an aryloxy group, an acyloxy group, an arylthio group, an alkylthio group, and $$-N\begin{pmatrix}Z_2\end{pmatrix}$$

in which $Z_2$ represents a group of atoms necessary to a 5- or 6-membered ring together with the nitrogen atom, provided, the atoms of the group are selected from the group consisting of carbon atom, oxygen atom, nitrogen atom and sulfur atom.

The typical examples thereof will be given below:

Halogen atoms: Chlorine atom, bromine atom and fluorine atom.

Alkoxy groups: An ethoxy group, a benzyloxy group, an ethylcarbamoylmethoxy group and a tetradecylcarbamoylmethoxy group.

Aryloxy groups: A phenoxy group, a 4-methoxyphenoxy group and a 4-nitrophenoxy group.

Acyloxy groups: An acetoxy group, a myristyloxy group and a benzoyloxy group.

Arylthio groups: A phenylthio group, a 2-butoxy-5-octylphenylthio group and a 2,5-dihexyloxyphenylthio group.

Alkylthio groups: A methylthio group, an actylthio group, a hexadecylthio group, a benzylthio group, a 2-(diethylamino)ethylthio group, an ethoxycarbonylmethylthio group, an ethoxyethylthio group and a phenoxyethylthio group.

The groups represented by $$-N\begin{pmatrix}Z_2\end{pmatrix}$$

include, for example, the following groups:

As X, halogen atoms are preferably used and, among the halogen toms, chlorine atom is particularly preferably used.

Now, Rhd 2 denoted in Formula I will be detailed.

Rhd 2 denoted in Formula I is further represented by Formula II and at least one of $R_1$ and Rhd 2 represents a secondary or tertiary alkyl group.

Next, Formula II will be detailed.

Rhd 3 through Rhd 6 denoted in formula II represent each a hydrogen atom or an alkyl group and they are synonymous with $R_1$ denoted in Formula I.

Further, Rhd 7 denoted in Formula II will be detailed.

Rhd 7 represents a univalent group having at least one of —COOM group in which M represents a hydrogen atom or a cation, and Rhd 7 is preferably represented by Formula III.

Now, Formula II will be detailed.

Formula III $$-(J_1)_m-(J_2)_n-(J_3)_p-(J_4)_q-R_8$$

wherein $J_1$ through $J_4$ represent each alkylene groups such as a methylene group, an ethylene group and a trimethylene group, arylene groups such as a phenylene group, and divalent groups such as

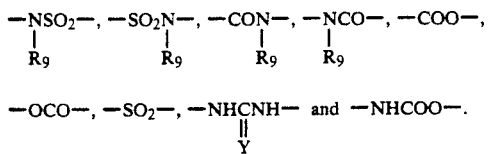

In the substituents, Rhd 9 represents a hydrogen atom, an alkyl group or an aryl group; and Y represents a hydrogen atom or a sulfur atom, provided, the above-given alkylene groups, arylene groups and Rhd 9 are further allowed to have a substituent. Such substituents include the same substituents as given in the case that $R_1$ denoted in the foregoing Formula I represents an alkyl group.

In Formula III, Rhd 8 represents each alkyl groups such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopentyl group and a cyclohexyl group; and aryl groups such as a phenyl group; provided, in this case, the alkyl and aryl groups are further allowed to have a substituent. Such substituents include, for example, the same as the substituents given in the case that $R_1$ denoted in the foregoing Formula I represents an alkyl group. The univalent groups represented by Formula III have each at least one of —COOM in which M represents a hydrogen atom or a cation. Such —COOM group can be introduced thereinto by directly or through a divalent group substituting them to $J_1$, $J_2$, $J_3$, $J_4$, and Rhd 8.

The typical examples of the magenta couplers relating to the invention will be given below. It is, however, to be understood that the invention shall not be limited thereto.

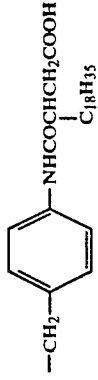

-continued

| No. | R₁ | X | R₂ |
|---|---|---|---|
| 8 | $CH_3$<br>$-C-COOC_2H_5$<br>$CH_3$ | Cl | $-CH_2CH_2-$⟨C₆H₄⟩$-NHSO_2-$⟨C₆H₃(OH)(COOH)⟩ |
| 9 | $-C(CH_3)_3$ | $-OC_3H_7$ | $-CH_2-$⟨C₆H₄(CH₃)⟩$-NHCOCHCH_2COOH$ / $C_{12}H_{25}$ |
| 10 | $-C(CH_3)_3$ | Cl | $-CH_2-$⟨C₆H₄⟩$-OCOCHCH_2COOH$ / $C_{12}H_{25}$ |
| 11 | $CH_3$<br>$-C-CH_2Cl$<br>$CH_3$ | Cl | $-CH_2CH_2-$⟨C₆H₄⟩$-NHCOCHCH_2COOH$ / $C_{12}H_{25}$ |
| 12 | $CH_3$<br>$-C-C_6H_5$<br>$CH_3$ | Cl | $-CH_2-$⟨C₆H₄⟩$-NHSO_2-$⟨C₆H₄-COOH⟩ |
| 13 | $CH_3$<br>$-C-C_3H_7$<br>$OCH_3$ | Cl | $-CH_2CH_2-$⟨C₆H₄⟩$-OCOCHCH_2COOH$ / $C_{10}H_{21}$ |
| 14 | $-C(CH_3)_3$ | Cl | $C_2H_5$<br>$-CH-$⟨C₆H₄⟩$-NHCOCHCH_2COOH$ / $C_{10}H_{21}$ |

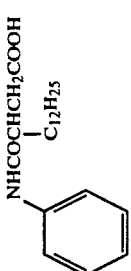

-continued

| No. | $R_1$ | X | $R_2$ |
|---|---|---|---|
| 23 | $OC_4H_9$<br>$-CHC_{12}H_{25}$ | Cl | 3-COOH-C$_6$H$_4$-NHSO$_2$-C$_6$H$_4$-CH(CH$_2$-)(C$_2$H$_5$) |
| 24 | $-CHC_2H_5$<br>$\;\;\;\;\;\vert$<br>$\;\;\;\;CH_3$ | Cl | 4-(OCOCHC$_{14}$H$_{29}$CH$_2$COOH)-C$_6$H$_4$-CH(C$_2$H$_5$)- |
| 25 | $-CH(CH_3)_2$ | Cl | 4-(NHCOCHC$_{18}$H$_{37}$CH$_2$COOH)-C$_6$H$_4$-CH(C$_2$H$_5$)- |
| 26 | $-CH(CH_3)_2$ | Cl | 4-(NHCOCHC$_{12}$H$_{25}$CH$_2$COOH)-C$_6$H$_4$-CH(CH$_3$)CH(CH$_3$)- |
| 27 | $-CH_3$ | Cl | 4-(NHCOCHC$_{18}$H$_{35}$CH$_2$COOH)-C$_6$H$_4$-CH(C$_2$H$_5$)- |
| 28 | $-CH_3$ | Cl | 4-(NHCOCHC$_{18}$H$_{35}$CH$_2$COOH)-C$_6$H$_4$-CH(C$_3$H$_7$)- |
| 29 | $-C_9H_{17}$ | Cl | 2-COOH-C$_6$H$_4$-O-C$_6$H$_4$-NHCO-... -CH(C$_2$H$_5$)- |

-continued

| No. | R$_1$ | X | R$_2$ |
|---|---|---|---|
| 30 | —C$_{15}$H$_{31}$ | Cl | 4-(CH(C$_2$H$_5$)-)phenyl-NHSO$_2$-(3-COOH-phenyl) |
| 31 | —CH$_3$ | Cl | 4-(CH(C$_2$H$_5$)-)phenyl-NHSO$_2$-(3-(NHCOCH(C$_{12}$H$_{25}$)CH$_2$COOH)-phenyl) |
| 32 | —CH$_3$ | Cl | 4-(CH(CH$_3$)(C$_2$H$_5$)-)phenyl-NHCOCH(C$_{12}$H$_{25}$)CH$_2$COOH |
| 33 | —CH$_3$ | Cl | 4-(CH(CH$_3$)(CH$_3$)-CH-)phenyl-OCO-CH(C$_{18}$H$_{37}$)CH$_2$COOH |
| 34 | —CH$_3$ | Cl | 4-(CH(CH$_3$)CH$_2$-)phenyl-NSO$_2$CH$_2$COOH (C$_{10}$H$_{25}$) |
| 35 | —CH$_3$ | Cl | 4-(CH(CH$_3$)CH$_2$-)phenyl-NHCOCH(C$_{18}$H$_{37}$)CH$_2$COOH |
| 36 | —C$_2$H$_4$Cl | Cl | 4-(CH(CH$_3$)CH$_2$-)phenyl-NHCOCH(C$_{12}$H$_{25}$)CH$_2$COOH |
| 37 | —CH$_2$—C$_6$H$_5$ | Cl | 4-(CH(C$_2$H$_5$)-)phenyl-NHSO$_2$-(3-(NHCOCH(C$_{12}$H$_{25}$)CH$_2$COOH)-phenyl) |

-continued

| No. | R₁ | X | R₂ |
|---|---|---|---|
| 38 | —CH₂C(CH₃)₃ | (1-benzyl-hydantoin-3-yl group) | 2-(4-(1-propylbutyl)phenyl)carbamoyl-benzoic acid residue (–NHCO–C₆H₄–CH(C₃H₇)– with COOH ortho) |
| 39 | 2-(t-C₅H₁₁)-4-(t-C₅H₁₁)-phenoxymethyl (—CH₂O–C₆H₃(C₅H₁₁(t))₂) | Cl | 3-(4-(2-methyl-2-butyl)phenyl)sulfonamido-benzoic acid residue (–NHSO₂–C₆H₄–C(CH₃)(C₂H₅)– with COOH meta) |
| 40 | —CH₂CH₂SO₂C₁₂H₂₅ | Cl | —NHCOCH₂CH₂COOH on 4-(1-methylpropyl)aniline (–C₆H₄–CH(CH₃)(C₂H₅)–NHCOCH₂CH₂COOH; R₂ = –CHCH₃ with C₂H₅) |
| 41 | —(CH₂)₃–C₆H₄–NHSO₂–C₆H₄–OC₁₂H₂₅ | Cl | —NHCOCH₂CH₂COOH on 4-(2-butyl)aniline (–CH(C₂H₅)–C₆H₄–NHCOCH₂CH₂COOH) |
| 42 | —CH₂OCH₃ | Cl | —NHCOCHCH₂COOH with C₁₂H₂₅ substituent on the α-carbon, on 4-(2-methyl-2-butyl)aniline (–C(CH₃)(C₂H₅)–C₆H₄–NHCOCH(C₁₂H₂₅)CH₂COOH) |

Next, an example of the syntheses of the compounds applicable to the invention will be given.

Example: Synthesis of Exemplified Compound 1

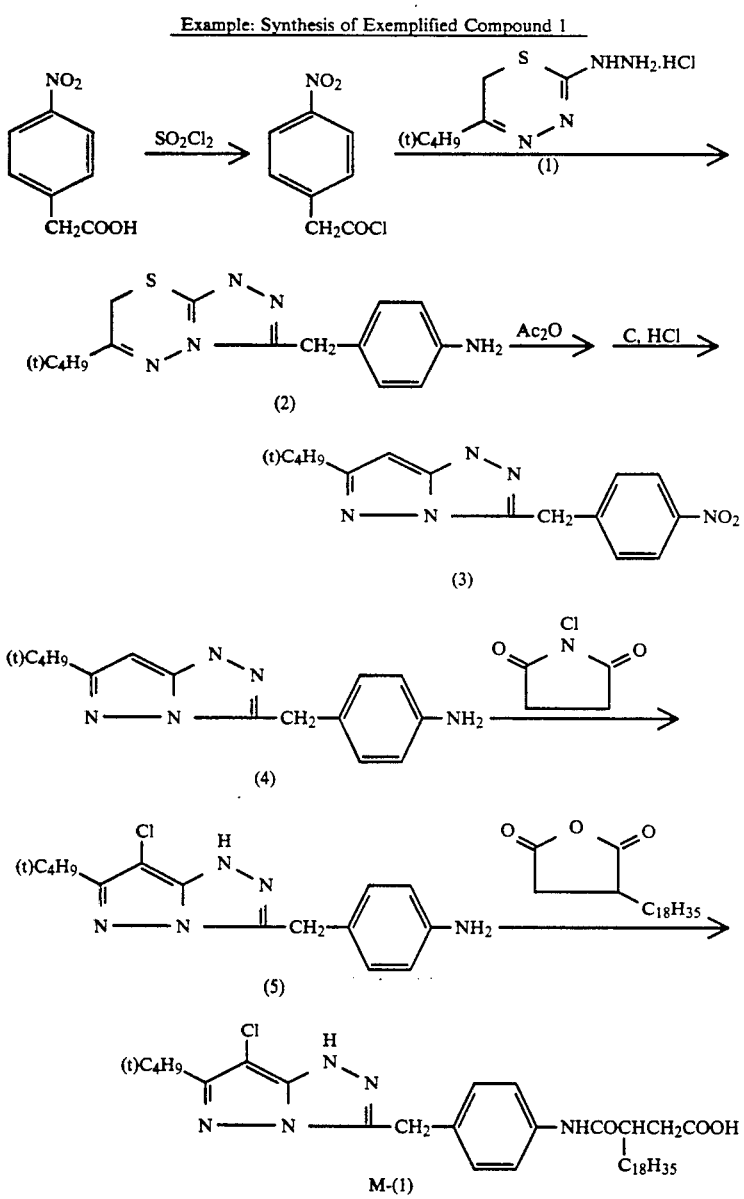

A reflux of 45 g of p-nitrophenyl acetic acid was made with heating for two hours in 50 ml of thionyl chloride and the thionyl chloride was then distilled off. Further, 52 g of compound (1) was added and the reflux thereof was made with heating for five hours. The resulting reacted mixture was filtrated with heating and the solvents were distilled off from the filtrates, so that a residue was obtained. The resulting residue was recrystallized with acetonitrile, so that 55 g of compound (2) was obtained.

Next, the reflux of 54 g of compound (2) was made with heating for two hours in 150 ml of anhydrous acetic acid and the solvents were distilled off, so that a residue was obtained. The resulting residue was added into 150 ml of methanol and 33 ml of concentrated hydrochloric acid was further added thereinto. The reflux of the resulting mixture was made with heating for two hours. The resulting sulfur was filtrated off and the solvents were then distilled off, so that a residue was obtained.

The resulting residue was dissolved with 500 ml of ethyl acetate and washed twice with warm water and once with brine. After the washed residue was dehydrated with anhydrous magnesium sulfate, the solvents were distilled off, so that a residue was obtained. The resulting residue was recrystallized with acetonitrile, so that 29 g of compound (3) was obtained.

Next, 28 g of compound (3) was dissolved in 500 ml of N,N-dimethylformamide and 120 ml of water and 120 ml of aqueous ammonia were added thereinto, and the resulting mixture was heated. Keeping the temperature to be about 50° C., 80 g of sodium hydrosulfite was added little by little. Thereafter, the mixture was cooled radiantwise with stirring and was then neutralized with 3N hydrochloric acid. After it was filtrated, the filtrate solution was poured into 2.5 l of water and was then extracted with ethyl acetate. After the ethyl acetate was distilled off, so that 16 g of compound (4) was obtained.

Next, compound 4 of 12 g was dissolved in the mixture of 120 ml of chloroform and 100 ml of N,N-dimethylformamide and 6 g of N-succinimide was added little by little thereinto with cooling with ice. Thereafter, the chloroform was distilled off and the resulting residue was poured into water. After extracting with ethyl acetate and the ethyl acetate was distilled off, a residue was obtained. The resulting residue was refined in column chromatography, so that 13 g of compound (5) was obtained.

Further, 7 g of compound (5) was added into ethyl acetate and 7.8 g of anhydrous octadecenyl succinic acid was then added. The reflux thereof was made with heating for one hour and the solvents were distilled off, so that a residue was obtained. The resulting residue was refined in a column chromatography, so that 6.8 g of Exemplified compound 1 was obtained.

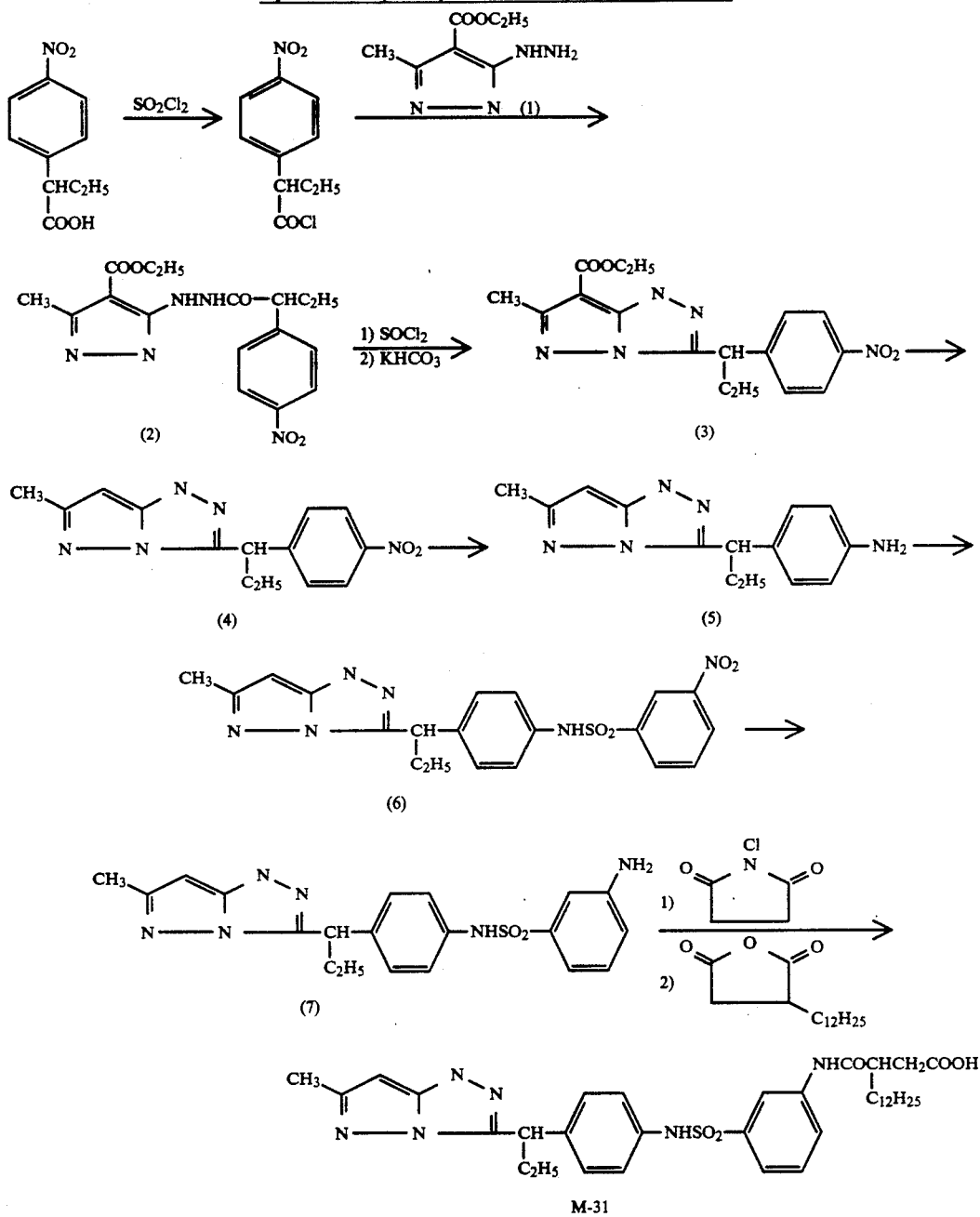

Synthesis Example 2: Synthesis of Exemplified compound 31

The reflux of 63 g of 2-(p-nitrophenyl) butylic acid was made with heating for two hours in 250 ml of thionyl chloride. After the thionyl chloride was distilled off, an acid chloride was obtained.

Compound (1) of 55 g was dispersed in 300 ml of ethyl acetate and 44 g of potassium acetate and 175 ml of water were further added thereinto. After it was stirred, the resulting acid chloride was dropped therein. After dropping the acid chloride, the mixture was stirred for two hours and a solid matter was obtained by filtration. After the solid matter was washed with water and then with a small amount of ethyl alcohol, 90 g of compound (2) was obtained.

Next, 90 g of compound (2) was added into 900 ml of ethyl acetate and 35 ml of thionyl chloride was added thereinto. The reflux of the resulting mixture was made with heating for two hours. After cooling it, 300 ml of water and 400 ml of ethyl acetate were added thereinto. After the mixture was stirred, an ethyl acetate layer was separated and washed until neutralized with a 10% potassium hydrogencarbonate solution. Thereafter, 48 g of potassium hydrogencarbonate and 200 ml of water were added to the ethyl acetate layer, and the reflux thereof was made with heating for 30 minutes. After cooling it, a solid matter was obtained by filtration. After drying it by the air, the solid matter was dispersed in acetonitrile and then filtrated. After the filtrate was refined, 60 g of compound (3) was obtained.

Further, the reflux of 50 g of compound (3) was made with heating for six hours in a mixture of 84 ml of acetic acid, 25 ml of water and 25 ml of concentrated sulfuric acid. After it was cooled, it was then poured into ice water and filtrated, so that a solid matter was obtained. After the solid matter was washed with water and was then dispersed in methanol, 28 g of compound (4) was obtained by filtration.

Compound (4) of 27 g was dissolved in 500 ml of N,N-dimethylformamide and 130 ml of water and 130 ml of aqueous ammonia were added thereinto. The resulting mixture was heated up to 50° C. and thereinto 80 g of sodium hydrosulfite was added little by little. Thereafter, the mixture was cooled down with stirring and was then neutralized with 3N hydrochloric acid. After filtrating, the filtrate was poured into 2.5 l of water and was then extracted with ethyl acetate. After distilling the ethyl acetate off, 12 g of compound (5) was obtained.

Compound (5) of 10 g and triethyl amine of 5 g were stirred in 80 ml of acetonitrile, and 9.2 g of m-nitrobenzenesulfonyl chloride was dropped thereinto. After dropping it, the mixture was further stirred for four hours and was then poured into 1 l of water. The resulting mixture was extracted with ethyl acetate and then the ethyl acetate was distilled off, so that 14 g of compound (6) was obtained.

Compound (6) of 14 g was reduced in the same processing steps as those for preparing compound (5) from compound (4), so that 5 g of compound (7) was obtained.

Compound (7) of 5 g was added into 30 ml of chloroform and 40 ml of tetrahydrofuran and, after 1.7 g of n-chlorosuccinimide was further added thereinto with cooling with ice, the solvents were distilled off and then washed by adding 50 ml of ethyl acetate. The solvents were distilled off from the resulting ethyl acetate layer, so that a residue was obtained. The residue was refined in chromatography, so that 3.2 g of a chlorinated compound was obtained. The reflux of 3.0 g of the chloride was made with heating for two hours with anhydrous dodecylsuccinic acid in 30 ml of ethyl acetate. The solvents were distilled off, so that a residue was obtained. The resulting residue was crystallised with acetonitril, so that 2.6 g of Exemplified compound 31 was obtained.

The couplers applicable to the invention may be used in an amount within the range of, normally, $1 \times 10^{-3}$ mols to 1 mol per mol of silver halide used and, preferably, $1 \times 10^{-2}$ mols to $8 \times 10^{-1}$ mols.

The coupler of the invention is preferably added to a green-sensitive silver halide emulsion layer.

The couplers of the invention may be used together with the other kinds of magenta couplers in combination, provided, the effects of the invention cannot be spoiled.

In the silver halide emulsions applicable to the invention, any one of the silver halides applicable to ordinary silver halide emulsions may be used, such as silver bromide, silver iodobromide, silver iodochloride, silver chlorobromide, silver chloroiodobromide and silver chloride Silver halide grains may be those having a uniform distribution of silver halide compositions therein or core/shell type grains having different silver halide compositions between the inside of the grains and the surface layer of the grains.

The silver halide grains may be those in which a latent image is formed mainly on the surfaces of the grains or those in which a latent image is formed mainly inside of the grains.

The silver halide grains may be those having regular crystal forms such as a cube, an octahedron and a tetradecahedron, or those having irregular crystal forms such as a globular form and a tabular form. These grains may have any ratios of {100} plane to {111} plane.

The grains may also have any complex crystal forms or may be a mixture of grains having various crystal forms.

The grain-sizes of the silver halide grains applicable thereto are within the range of 0.05 to 30 $\mu$ and, preferably, 0.1 to 20 $\mu$.

The silver halide emulsions may be used regardless of any grain-size distributions. In other words, it is allowed either to use emulsions each having a wide grain-size distribution (hereinafter referred to as polydisperse type emulsions) or to use emulsions each having a narrow grain-size distribution (hereinafter referred to as monodisperse type emulsions) independently or in combination.

It is further allowed to use the polydisperse type emulsions and monodisperse type emulsions in a mixture form. The couplers applicable to the invention include colored couplers each having a color compensation effect and compounds capable of releasing photographically useful fragments such as a development inhibitor, a development accelerator, a bleach accelerator, a developing agent, a silver halide solvent, a color toner, a hardener, a foggant, an antifoggant, a chemical sensitizer, a spectral sensitizer and a desensitizer, upon coupling reaction with the oxidized products of a developing agent.

Among the above-given compounds, it is also allowed to use the so-called DIR compounds which are capable of releasing a development inhibitor with processing a development and improving the sharpness and graininess of images.

The above-mentioned DIR compounds include those in which an inhibitor is directly coupled to the coupling position, and those in which an inhibitor is coupled to the coupling position through a divalent group so as to release the inhibitor upon intramolecular nucleophilic reaction or intramolecular electron-transfer reaction produced in a group having been split off by a coupling reaction, which is so called as timing DIR compounds. On the other hand, it is allowed either to use an inhibitor capable of displaying a diffusibility after it was split off or to use an inhibitor not so diffusible, independently or in combination to meet the purposes of application.

It is also allowed to use a colorless coupler capable of making a coupling reaction with the oxidized products of an aromatic primary amine developing agent, but incapable of forming any dye, which is called sometimes as a competing coupler, and a dye-forming coupler in combination.

The yellow couplers applicable to the invention preferably include well-known acylacetanilide type couplers. Among these couplers, benzoylacetanilide type and pivaloylacetanilide type compounds may advantageously be used.

As for the cyan couplers applicable to the invention, a phenol and naphthol types couplers may generally be used.

It is allowed to use an anti-color-foggant for preventing a color contamination, a sharpness deterioration and a rough graininess, which may be produced by the oxidized products of a developing agent or an alectron-transferring agent transferring from and to the emulsions, each having the same or different color sensitivity, of a light-sensitive material.

An image stabilizer can be used in a light-sensitive material, for preventing a dye-image deterioration. The compounds preferably applicable are given in DR 17643, Paragraph VII, Item J.

In light-sensitive materials, the hydrophilic colloidal layers thereof such as a protective layer and an interlayer are allowed to contain a Uv absorbent for preventing a fog production caused by an electric discharge generated by a frictional charge on the light-sensitive material, and for preventing an image deterioration caused by UV rays.

A formalin scavenger may be used in light-sensitive materials for preventing a magenta dye-forming coupler from being deteriorated by a formalin during the storage of the light-sensitive materials.

The invention can preferably be applied in color negative films, color papers and color reversal films, for example.

Generally, such color negative films, color papers and color reversal films are comprised of each of blue-, green- and red-sensitive silver halide emulsion layers and non-light-sensitive hydrophilic colloidal layers, and the invention shall not be limited at all to the arrangements of these layers on a support. For obtaining a dye image on the light-sensitive material of the invention, an exposure is made to light and a color development processing is then carried out.

The color processing is comprised of a color developing step, a bleaching step, a fixing step, a washing step and, if required, a stabilizing step. It is also allowed to carry out a bleach-fixing step with the use of a monobath type bleach-fixer, in place of both of the step of using a bleacher and the step of using a fixer. It is further allowed to carry out a monobath type processing step of using a monobath type developing, bleaching and fixing solution for color development, bleaching and fixation.

EXAMPLES

EXAMPLE 1

Each of Samples 1 through 11 was prepared in the following manner:

As shown in Table-1, a magenta coupler of the invention or a comparative coupler was taken in an amount of 0.1 mols per mol of silver. Tricresyl phosphate in the same amount as much as the amount by weight of the couplers and ethyl acetate in an amount three times as much as the amount by weight of the couplers were added thereto. The resulting mixture was heated up to 60° C. so as to be dissolved completely.

The resulting solution was mixed up with 1200 ml of an aqueous 5% gelatin solution containing 120 ml of an aqueous 5% solution of Alkanol B, that is, alkylnaphthalene sulfonate manufactured by DuPont. The mixture was dispersed to be emulsified with a supersonic homogenizer, so that a dispersion was obtained. Next, the resulting dispersion was added into 4 kgs of a green-sensitive silver iodobromide emulsion containing 6 mol % of silver iodide, and 120 ml of a 2% 1,2-bis(vinylsulfonyl)ethane solution containing water and methanol in a proportion of 1:1 was added as a hardener. The resulting coating solution was coated over to a subbed transparent polyester base and dried, so that each of the samples was prepared. Amount of silver coated was 20 mg/100 cm$^2$.

The resulting samples were exposed to light through an optical wedge in an ordinary method and then processed in the following steps.

Thus obtained magent images were subjected to densitometry by a densitometer with green light.

The results thereof are shown in Table-1.

| <Processing steps> | | |
|---|---|---|
| Color developing | 38° C. | 3 min. 15 sec. |
| Bleaching | 38° C. | 4 min. 20 sec. |
| Washing | 38° C. | 3 min. 15 sec. |
| Fixing | 38° C. | 4 min. 20 sec. |
| Washing | 38° C. | 3 min. 15 sec. |
| Stabilizing | 38° C. | 1 min. 30 sec. |
| Drying | 47° C. ± 5° C. | 16 min. 30 sec. |

The compositions of the processing solutions used in the above processing steps were as follows:

| <Composition of Color Developer> | |
|---|---|
| Potassium carbonate | 30.0 g |
| Sodium hydrogencarbonate | 2.5 g |
| Potassium sulfite | 5.0 g |
| Potassium bromide | 1.3 g |
| Potassium iodide | 2.0 g |
| Hydroxylamine sulfate | 2.5 g |
| Sodium chloride | 0.6 g |
| Sodium diethylenetriamine pentaacetate | 2.5 g |
| 3-methyl-4-amino-N-ethyl-N-($\beta$-hydroxyethyl) aniline sulfate | 4.8 g |
| Potassium hydroxide | 1.2 g |
| Add water to make in total | 1 liter |
| Adjust pH with potassium hydroxide or an aqueous 20% sulfuric acid solution to be | pH 10.06 |
| <Composition of Bleacher> | |
| Ferric-ammonium ethylenediaminetetraacetate | 100.0 g |
| Sodium ethylenediaminetetraacetate | 10.0 g |
| Ammonium bromide | 150.0 g |
| Glacial acetic acid | 40.0 ml |
| Sodium bromide | 10.0 g |
| Add water to make | 1 liter |
| Adjust pH with an aqueous ammonia or glacial acetic acid to be | pH 3.5 |
| <Composition of Fixer> | |
| Ammonium thiosulfate | 180.0 g |
| Sodium sulfite. anhydrous | 12.0 g |
| Sodium metabisulfite | 2.5 g |
| Disodium ethylenediaminetetraacetate | 0.5 g |
| Sodium carbonate | 10.0 g |
| Add water to make | 1 liter |
| <Composition of Stabilizer> | |
| Formalin, in an aqueous 37% solution | 2.0 g |
| Konidux, manufactured by Konica Corporation | 5.0 g |

-continued

| | |
|---|---|
| Add water to make | 1 liter |

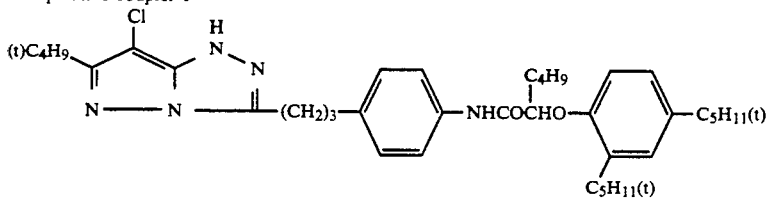

Comparative coupler-1

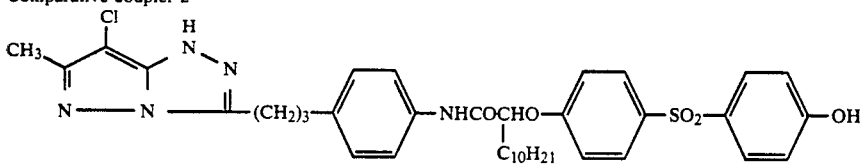

Comparative coupler-2

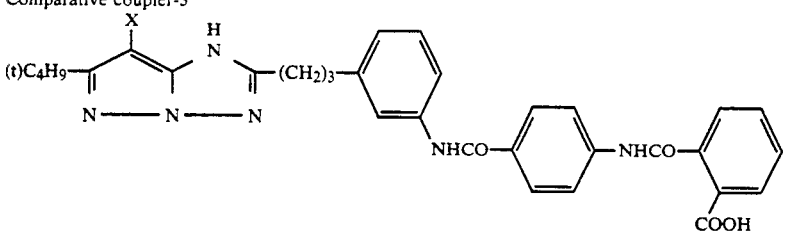

Comparative coupler-3

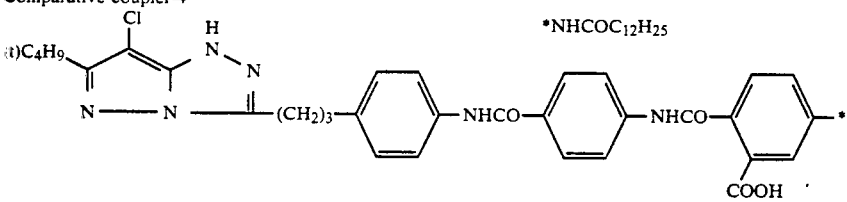

Comparative coupler-4

TABLE-1

| Sample No. | Coupler | Specific sensitivity[1] | Max density | Color-tone variation[2] |
|---|---|---|---|---|
| 1 Comparative | Comparative 1 | 100 | 1.52 | 98 |
| 2 Comparative | Comparative 2 | 130 | 2.40 | 94 |
| 3 Comparative | Comparative 3 | 143 | 2.57 | 98 |
| 4 Comparative | Comparative 4 | 138 | 2.49 | 98 |
| 5 Invention | Exemplification 1 | 178 | 2.94 | 99 |
| 6 Invention | Exemplification 2 | 170 | 2.88 | 99 |
| 7 Invention | Exemplification 3 | 182 | 2.98 | 99 |
| 8 Invention | Exemplification 18 | 160 | 2.69 | 99 |
| 9 Invention | Exemplification 31 | 190 | 2.05 | 98 |
| 10 Invention | Exemplification 32 | 188 | 3.00 | 99 |
| 11 Invention | Exemplification 7 | 168 | 2.71 | 99 |

[1] Each specific sensitivity value is the reciprocal of an exposure capable to giving a density of a fog density + 0.1 and is expressed by a value relative to that of the sample containing comparative coupler 1 which is regarded as a value of 100.

[2] Color tone variation is calculated by the following equation:

$$\frac{A_{max-25}^{0.5}/A_{max}^{0.5} \times 100}{A_{max-25}^{1.5}/A_{max}^{1.5}}$$

wherein $A_{max}^{0.5}$ and $A_{max}^{1.5}$ are absorbances at the maximum absorption wavelength of images having the densities of 0.5 and 1.5, respectively, and $A_{max-25}^{0.5}$ and $A_{max-25}^{1.5}$ are absorbances at the wavelength of 25 mm shorter than the maximum absorption wavelength of the images having the densities of 0.5 and 1.5, respectively.

As is obvious from Table-1, it was confirmed that the samples relating to the invention were high in the maximum density without lowering the sensitivities and less in color tone differences caused by density variations of image.

EXAMPLE 2

A multilayered color light-sensitive material was prepared by coating the following layers in order over a polyethylene resin coated paper containing anatase type titanium oxide.

The amounts of the contents added in the light-sensitive material are shown by the amounts each per 100 cm².

(1) A layer containing 20 mg of gelatin, a blue-sensitive silver chlorobromide emulsion containing 5 mg of silver that was containing 80 mol % of silver bromide, 8 mg of yellow coupler, 0.1 mg of 2,5-di-t-octyl hydroquinone, and 3 mg of dioctyl phthalate;

(2) A layer containing 12 mg of gelatin, 0.5 mg of 2,5-di-t-octyl hydroquinone, 4 mg of a mixture of UV-1 and UV-2 in a mixing ratio of 1:1, and 2 mg of dibutyl phthalate;

(3) A layer containing 18 mg of gelatin, a green-sensitive silver chlorobromide emulsion containing 4 mg of silver that was containing 70 mol % of silver bromide, 5 mg of magenta coupler, 2 mg of di-t-pentyl hydroquinone-di-octyl ether, 0.2 mg of 2,5-di-t-octyl hydroquinone, and 2.5 mg of dioctyl phthalate;

(4) An interlayer containing the same compositions as in layer 2);

(5) A layer containing 16 mg of gelatin, a red-sensitive silver chlorobromide emulsion containing 4 mg of silver that was containing 70 mol % of silver bromide, 3.5 mg of cyan coupler*, 0.1 mg of 2,5-di-t-octyl hydroquinone, and 2.0 mg of tricresyl phosphate; and (6) A protective layer containing 9 mg of gelatin.

The multilayered light-sensitive material was exposed to light through an optical wedge in an ordinary method and was then treated in the following development process.

The yellow, magenta and cyan couplers each used in the respective layers and the results of processing the light-sensitive material are shown in Table-2.

The magenta density of each sample was measured by a densitometer with green light after the samples were exposed to white light and processed by the following procedure.

| <Processing steps> | | |
|---|---|---|
| Color developing | 38° C. | 3 min. 30 sec. |
| Bleach-fixing | 38° C. | 1 min. 30 sec. |
| Stabilizing/or washing | 25~30° C. | 3 min. |
| Drying | 75~80° C. | 2 min. |

The compositions of the processing solutions used in each of the processing steps were as follows:

| <Color Developer> | |
|---|---|
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-methyl-4-amino-N-ethyl-N-(β-methanesulfonamidoethyl)aniline sulfate | 5.5 g |
| Fluorescent whitening agent, a 4,4'-diaminostilbene disulfonic acid derivative | 1.0 g |
| Potassium hydroxide | 2.0 g |
| Add water to make in total of | 1 liter |
| Adjust pH to be | pH 11.08 |
| <Bleach-fixer> | |
| Ferric ammonium ethylenediamine-tetraacetate dihydrate | 60 g |
| Ethylenediaminetetraacetic acid | 3 g |
| Ammonium thiosulfate, in a 70% solution | 100 ml |
| Ammonium sulfite, in a 40% solution | 27.5 ml |
| Glacial acetic acid | 10.0 ml |
| Adjust pH with potassium carbonate or glacial acetic acid to be | pH 7.1 |
| Add water to make in total of | 1 liter |
| <Stabilizer> | |
| 5-chloro-2-methyl-4-isothiazoline-3-one | 1.0 g |
| 1-hydroxyethylidene-1,1-disulfonic acid | 2.0 g |
| Add water to make | 1 liter |
| Adjust pH with silfuric acid or potassium hydroxide to be | pH 7.0 |

UV absorbents
UV-1

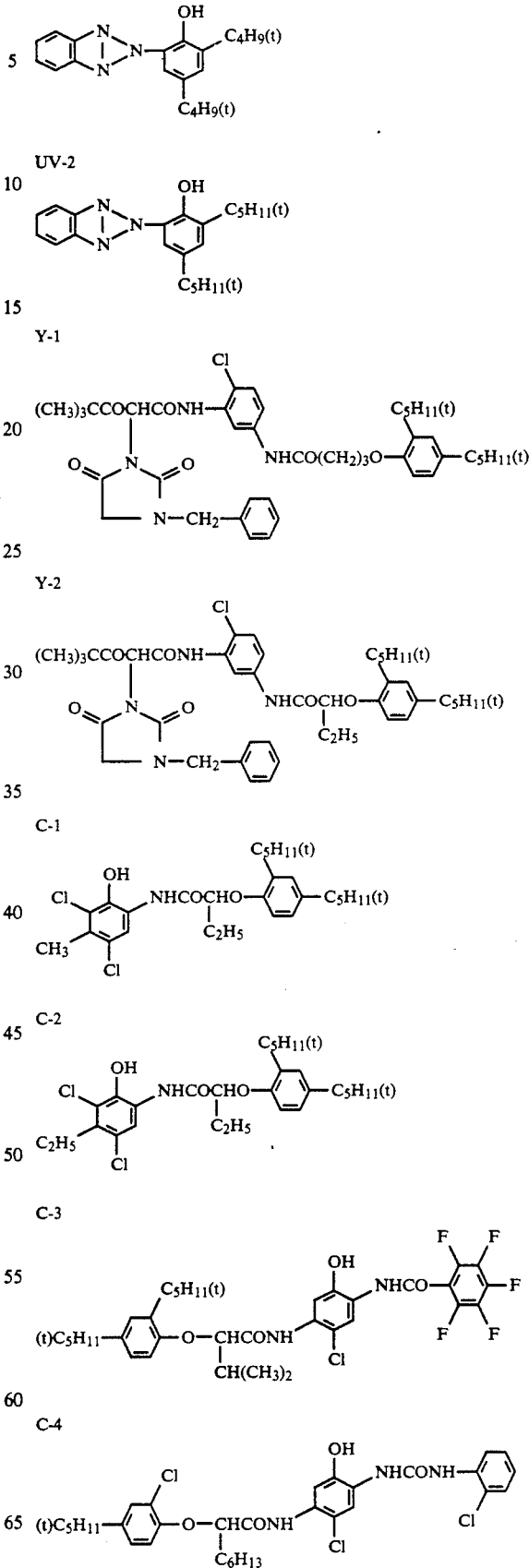

TABLE 2

| Sample No. | | Layer 1 Yellow coupler | Layer 3 Magenta coupler | Layer 5 Cyan coupler | Layer 5 UV absorbent | Specific sensitivity[1] | Maximum density | Tone variation | Light resistance[2] | Remarks |
|---|---|---|---|---|---|---|---|---|---|---|
| Comparative Sample | 201 | Y-1 | Comparative 3 | C-1 | — | 100 | 2.39 | 97 | 70 | |
| | 202 | Y-1 | Comparative 3 | C-1 | UV-1, UV-2 | 101 | 2.40 | 97 | 83 | Layer 5 was further added with 2 mg of UV absorbent |
| Inventive Sample | 203 | Y-1 | Exemplified 1 | C-1 | — | 124 | 2.76 | 99 | 80 | |
| | 204 | Y-1 | Exemplified 1 | C-1 | UV-1, UV-2 | 125 | 2.78 | 99 | 92 | |
| | 205 | Y-2 | Exemplified 2 | C-2 | UV-1, UV-2 | 121 | 2.69 | 99 | 82 | |
| | 206 | Y-2 | Exemplified 2 | C-2 | UV-1, UV-2 | 120 | 2.70 | 99 | 95 | The same layer as Layer 2 was coated between Layer 5 and Layer 6 each of Sample 205 |
| | 207 | Y-1 | Exemplified 3 | C-3 | UV-1, UV-2 | 129 | 2.77 | 99 | 84 | |
| | 208 | Y-1 | Exemplified 3 | C-3 | UV-1, UV-2 | 130 | 2.80 | 99 | 95 | The same layer arrangement as in Sample 206 |
| | 209 | Y-2 | Exemplified 32 | C-4 | UV-1, UV-2 | 134 | 2.83 | 99 | 78 | |

(1) Each specific sensitivity value is the reciprocal of an exposure capable to giving a density of a fog density + 0.11 and is expressed by a value relative to that of sample 201 containing comparative coupler which is regarded as a value of 100.

(2) The dye residual percentages at the portion of the sample having the initial density D=1.0 are shown in condition that, after the samples were color processed, they were irradiated with a xenon fade-o-meter for five days.

$$\text{Light resistance} = \frac{\text{Density obtained after irradiating for 5 days with xenon fade-o-meter}}{1.0} \times 100 \%$$

(3) The definition of the color tone variation is the same as in Example 1.

From the results shown in Table-2, it was confirmed that the samples relating to the invention are high in maximum density without lowering sensitivity and less in tone difference caused by density variations.

It was also proved that the dye images obtained in the invention are excellent in light resistance.

EXAMPLE 3

Over a triacetyl cellulose film support, each of the layers having the following composition was coated in order from the support, so that multilayered color photographic light-sensitive material sample No. 301 was prepared.

The amount of the contents added into the silver halide photographic light-sensitive material are shown by the amounts eac per 1 m², unless otherwise expressly indicated.

The amount of silver halides and colloidal silver are expressed in terms of the silver contents.

| | |
|---|---|
| Layer 1: | An antihalation layer. HC |
| | A gelatin layer containing black colloidal silver |
| Layer 2: | An interlayer, IL |
| | A gelatin layer containing an emulsified dispersion of 2,5-di-t-octyl hydroquinone |
| Layer 3: | A low-speed red-sensitive silver halide emulsion layer, RL |
| | Monodisperse type emulsion, Em I, having an average grain-size of 0.30 μm, which comprised AgBrI containing 6.0 mol % of AgI — Amount of silver coated: 1.8 g/m² |
| | Sensitizing dye I — 6 × 10⁻⁵ mols per mol of silver |
| | Sensitizing dye II — 1.0 × 10⁻⁵ mols per mol of silver |
| | Cyan coupler, C-2 — 0.06 mols per mol of silver |
| | Colored cyan coupler, CC-1 — 0.003 mols per mol of silver |
| | DIR compound, D-1 — 0.0015 mols per mol of silver |
| | DIR compound, D-2 — 0.002 mols per mol of silver |
| Layer 4: | A high-speed red-sensitive silver halide emulsion layer, RH |
| | Monodisperse type emulsion, Em II, having an average grain-size of 0.5 μm, which comprised AgBrI containing 7.0 mol % of AgI — Amount of silver coated: 1.3 g/m² |
| | Sensitizing dye I — 3 × 10⁻⁵ mols per mol of silver |
| | Sensitizing dye II — 1.0 × 10⁻⁵ mols per mol of silver |
| | Cyan coupler, C-5 — 0.02 mols per mol of silver |
| | Colored cyan coupler, CC-1 — 0.0015 mols per mol of silver |
| | DIR compound, D-2 — 0.001 mols per mol of silver |
| Layer 5: | An interlayer, IL |
| | A gelatin layer having the same composition as in Layer 2 |
| Layer 6: | A low-speed green-sensitive silver halide emulsion layer GL |
| | Em I — Amount of silver coated: 1.5 g/m² |

|   |   |   |
|---|---|---|
| | -continued | |
| | Sensitizing dye III | $2.5 \times 10^{-5}$ mols per mol of silver |
| | Sensitizing dye IV | $1.2 \times 10^{-5}$ mols per mol of silver |
| | Magenta coupler M-1 | 0.050 mols per mol of silver |
| | Colored magenta coupler CM-1 | 0.009 mols per mol of silver |
| | DIR compound D-1 | 0.0010 mols per mol of silver |
| | DIR compound D-3 | 0.0030 mols per mol of silver |
| Layer 7: | A high-speed green-sensitive silver halide emulsion layer GH | |
| | Em II | Amount of silver coated: 1.4 g/m² |
| | Sensitizing dye III | $1.5 \times 10^{-5}$ mols per mol of silver |
| | Sensitizing dye IV | $1.0 \times 10^{-5}$ mols per mol of silver |
| | Magenta coupler M-1 | 0.020 mols per mol of silver |
| | Colored magenta coupler CM-1 | 0.002 mols per mol of silver |
| | DIR compound D-3 | 0.0010 mols per mol of silver |
| Layer 8: | A yellow filter layer A gelatin layer containing of a yellow colloidal silver and 2,5-di-t-octyl hydroquinone | |
| Layer 9: | A low-speed blue-sensitive silver halide emulsion layer BL | |
| | Monodisperse type emulsion, Em-III, having an average grain-size of 0.48 μm, which comprised AgBrI containing 6 mol % of AgI | Amount of silver coated: 0.9 g/m² |
| | Sensitizing dye V | $1.3 \times 10^{-5}$ mols per mol of silver |
| | Yellow coupler Y-3 | 0.29 mols per mol of silver |
| Layer 10: | A high-speed blue-sensitive emulsion layer BH | |
| | Monodisperse type emulsion, Em IV, having an average grain-size of 0.8 μm, which comprised AgBrI containing 15 mol % of AgI | Amount of silver coated: 0.5 g/m² |
| | Sensitizing dye V | $1.0 \times 10^{-5}$ mols per mol of silver |
| | Yellow coupler Y-3 | 0.08 mols per mol of silver |
| | DIR compound D-2 | 0.0015 mols per mol of silver |
| Layer 11: | The first protective layer Pro-1 A gelatin layer containing | |
| | AgBrI containing 1 mol % of AgI and having an average grain-size of 0.7 μm UV absorbents, UV-1 and UV-2, in proportion of 1:1 | Amount of silver coated: 0.5 g/m² |
| Layer 12: | The second protective layer, Pro-2 A gelatin layer containing | |
| | Polymethyl methacryalate particles having an average particle-size of 1.5 μm Formalin scavenger, HS-1 | |

Besides the above-given compositions, a gelatin hardener H-1 and surface active agents were added to each of the layers.

Further, Samples Nos. 302 to 310 were prepared in the same manner as in Sample No. 301, except that M-1 contained in Lyaers 6 and 7 of Sample No. 301 were replaced by the couplers shown in Table-2.

The compounds contained in each of the layers of each sample were as follows:

Sensitizing dye I: Anhydro-5,5'-dichloro-9-ethyl-3,3'-di-(3-sulfopropyl)thiacarbocyanine hydrodie.

Sensitizing dye II: Anhydro-9-ethyl-3,3'-di-(3-sulfopropyl)-4,5,4',5'-dibenzothiazcarbocyanine hydroxide.

Sensitizing dye III: Anhydro-5,5'-diphenyl-9-ethyl-3,3'-di(3-sulfopropyl)oxacarbocyanine hydroxide.

Sensitizing dye IV: Anhydro-9-ethyl-3,3'-di-(3-sulfopropyl)-5,6,5',6'-dibenzooxacarbocyanine hydroxide.

Sensitizing dye V: Anhydro-3,3'-di-(3-sulfopropyl)-4,5-benzo-5'-methoxythiazyanine hydroxide.

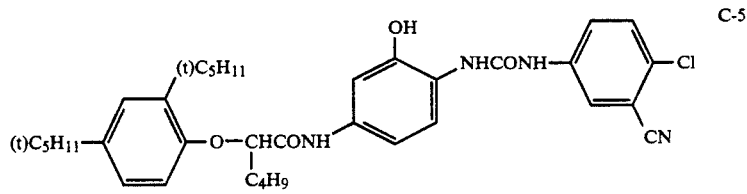

C-5

-continued
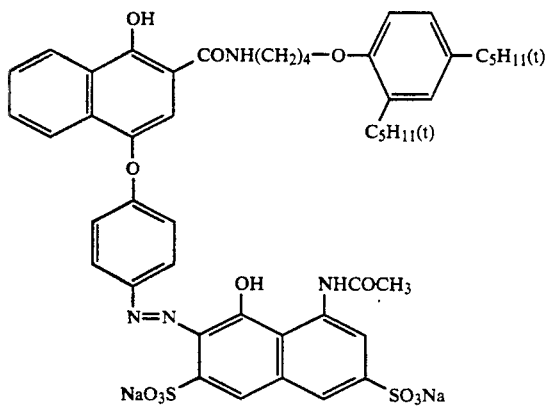
CC-1
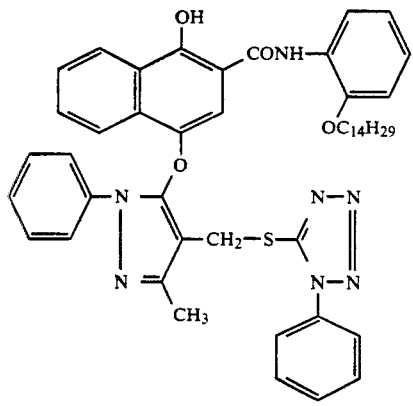
D-1
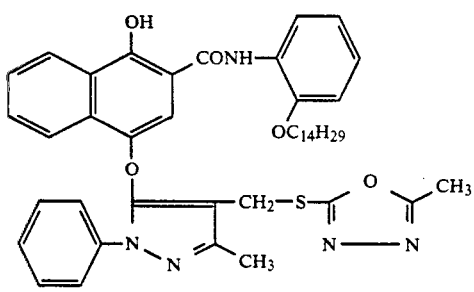
D-2
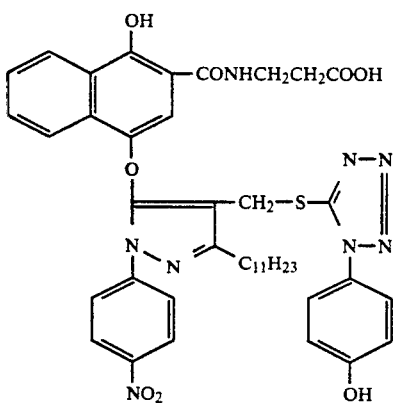
D-3
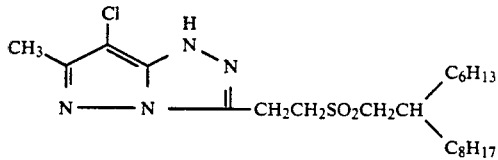
M-1

CM-1

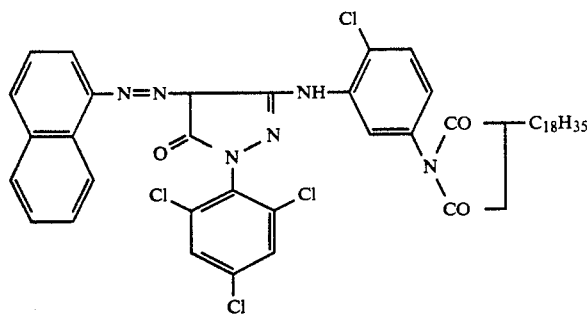

Y-3

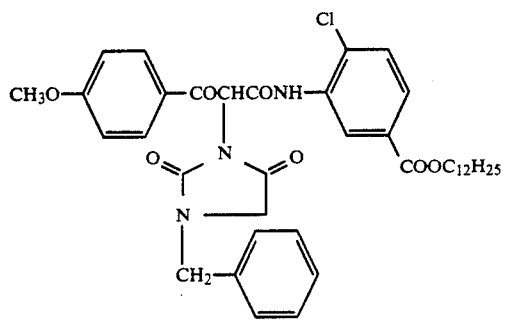

HS-1

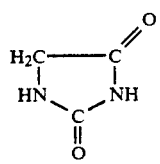

H-1

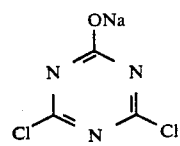

The resulting samples Nos. 301 through 310 were each exposed wedgewise to white light and were then treated in the following development process I.

| <Processing steps I> at 38° C. | Processing time |
|---|---|
| Color developing | 3 min. 15 sec. |
| Bleaching | 6 min. 30 sec. |
| Washing | 3 min. 15 sec. |
| Fixing | 6 min. 30 sec. |
| Washing | 3 min. 15 sec. |
| Stabilizing | 1 min. 30 sec. |
| Drying | |

The compositions of the processing solutions used in the above processing steps were as follows:

| <Color developer> | |
|---|---|
| 4-amino-3-methyl-N-ethyl-N-(β-hydroxylethyl)-aniline sulfate | 4.75 g |
| Sodium sulfite anhydride | 4.25 g |
| Hydroxylamine ½ sulfate | 2.0 g |
| Potassium carbonate anhydride | 37.5 g |
| Sodium bromide | 1.3 g |
| Trisodium nitrilotriacetate monohydrate | 2.5 g |
| Potassium hydroxide | 1.0 g |
| Add water to make | 1 liter |
| Adjust pH with potassium hydroxide or a 20% sulfuric acid solution to be | pH 10.06 |
| <Bleacher> | |

| -continued | |
|---|---|
| Ferric-ammonium ethylenediaminetetraacetate | 100.0 g |
| Diammonium ethylenediaminetetraacetate | 10.0 g |
| Ammonium bromide | 150.0 g |
| Glacial acetic acid | 10 ml |
| Add water to make | 1 liter |
| Adjust pH with aqueous ammonia to be | pH 6.0 |
| <Fixer> | |
| Ammonium thiosulfate | 175.0 g |
| Sodium sulfite anhydride | 8.5 g |
| Sodium metasulfite | 2.3 g |
| Add water to make | 1 liter |
| Adjust pH with acetic acid to be | pH 6.0 |
| <Stabilizer> | |
| Formalin, in an aqueous 37% solution | 1.5 ml |
| Konidux, manufactured by Konica Corporation | 7.5 ml |
| Add water to make | 1 liter |

Development process II was carried out in the same manner as in development process I, except that the pH value of the color developer used in development process I was adjusted to be a value of 9.76.

The results thereof are shown in Table-3.

TABLE-3

| Sample No. | Magenta coupler | Specific sensitivity[1] | Maximum density[2] | Tone variation[4] | Process variation[3] |
|---|---|---|---|---|---|
| 301 | Comparative 1 | 100 | 1.63 | 98 | 62 |
| 302 | Comparative 2 | 133 | 2.61 | 95 | 82 |

TABLE-3-continued

| Sample No. | Magenta coupler | Specific sensitivity[1] | Maximum density[2] | Tone variation[4] | Process variation[3] |
|---|---|---|---|---|---|
| 303 | Comparative 3 | 146 | 2.71 | 98 | 73 |
| 304 | Comparative 4 | 142 | 2.64 | 98 | 69 |
| 305 | Exemplified 1 | 172 | 2.97 | 99 | 92 |
| 306 | Exemplified 2 | 183 | 3.05 | 99 | 93 |
| 307 | Exemplified 3 | 164 | 2.85 | 99 | 94 |
| 308 | Exemplified 18 | 162 | 2.81 | 99 | 92 |
| 309 | Exemplified 32 | 189 | 3.11 | 98 | 94 |
| 310 | Exemplified 16 | 170 | 2.91 | 99 | 93 |

[1] The specific sensitivity is the reciprocal value of an exposure capable of giving a density of fog density + 0.1, which is a value relative to the value of Sample No. 301 that is regerded as a value of 100.
[2] The values of the specific sensitivity, maximum density and tone variation are the measured in development process I.
[3] Processing variations are obtained in the following formula:
$$\frac{\text{Maximum density of a sample treated in Process II}}{\text{Maximum density of a sample treated in Process I}} \times 100(\%)$$
[4] The definition of tone variations is the same as in Example 1.

As is obvious from the results shown in Table-3, it was proved that the couplers used in the invention are excellent in color developability, less in tone variation caused by a density variation, and capable of obtaining a sufficient color density even with a low pH color developer, as compared to the comparative couplers.

What is claimed is:

1. A silver halide photographic light-sensitive material comprising a support having thereon a silver halide emulsion layer containing a magenta coupler represented by the following Formula I:

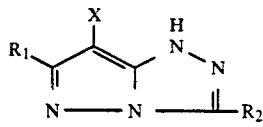

wherein $R_1$ is a primary-alkyl group, a secondary-alkyl group or a tertiary alkyl group; $R_2$ is an aralkyl group represented by the following Formula II; X is a substituent capable of splitting-off upon reaction with he oxidation product of a color developing agent;

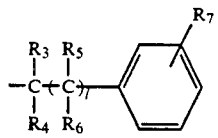

wherein $R_3$, Rhd 4, $R_5$ and $R_6$, are each a hydrogen atom or an alkyl group, provided that at least one of $R_3$ and $R_4$ is an alkyl group when $R_1$ is a primary-alkyl group; $R_7$ is a group having a —COOM group, in which M is a hydrogen atom or a cation; and l is 0 or 1.

2. A material of claim 1, wherein said alkyl group represented $R_1$ is a methyl group, an iso-propyl group or a tertiary-butyl group.

3. A material of claim 1, wherein aid substituent represented by X is a halogen atom, an alkoxy group, an aryloxy group, an acyloxy group, an arylthio group, an alkylthio group or

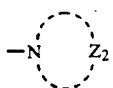

group in which $Z_2$ is a group of atoms, which are selected from a carbon atom, a nitrogen atom, an oxygen atom and a sulfur atom, necessary to form a five- or six-member heterocyclic ring.

4. A material of claim 3, wherein said substituent represented by X is a chlorine atom.

5. A material of claim 1, wherien said group represented by $R_7$ is a group represented by the following Formula III:

$$-(J_1)_m-(J_2)_n-(J_3)_p-(J_4)_q-R_8 \qquad III$$

wherein $J_1$, $J_2$, $J_3$ and $J_4$ are each an alkylene group, an arylene group, a

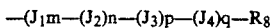

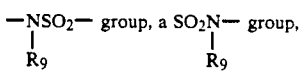

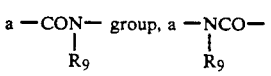

group, a —COO— group, a —COC— group, a —SO₂— group, a

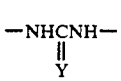

group or a —NHCOO— group in which $R_9$ is a hydrogen atom, an alkyl group or an aryl group; Y is a oxygen atom or a sulfur atom; $R_8$ represents a substituted or unsubstituted alkyl or aryl gorup; provided that at least one of said groups represented by $R_8$, $R_9$, $J_1$, $J_2$, $J_3$ and $J_4$ has a —COOm group or a substituent having a COOM group, M is a hydrogen atom or a cation; and m, n, p and q are each 0 or 1.

6. A material of claim 1, wherein said silver halide emulsion layer is a green-sensitive silver halide emulsion layer.

7. A material of claim 1, wherein said silver halide emulsion layer contains said coupler in an amount of from $1 \times 10^{-3}$ moles to 1 mole per mole of silver contained in said silver halide emulsion layer.

8. A material of claim 7, wherein said silver halide emulsion layer contains said coupler in an amount of from $1 \times 10^{-3}$ moles to $8 \times 10^{-1}$ moles per mole of silver contained in said silver halide emulsion layer.

* * * * *

UNITED STATES PATENT AND TRADEMARK OFFICE
CERTIFICATE OF CORRECTION

PATENT NO. : 5,071,739

DATED : December 10, 1991

INVENTOR(S) : Hidenobu Ohya et al.

It is certified that error appears in the above-identified patent and that said Letters Patent is hereby corrected as shown below:

Abstract, line 3, change "couler" to --coupler--.

Abstract, line 12, change "whrein" to --wherein--.

Claim 1, column 39, line 41, change "he" to --the--.

Claim 1, column 39, line 50, change "Rhd 4" to --$R_4$--.

Claim 3, column 40, line 1, change "aid" to --said--.

Claim 5, column 40, line 15, change "wherien" to --wherein--.

Claim 5, column 40, line 19, change "($J_1$m" to --($J_1$)m--.

Claim 5, column 40, line 39, before "oxygen" change "a" to --an--.

Claim 5, column 40, line 41, change "gorup" to --group--.

Claim 5, column 40, line 43, change "$COO_m$" TO --COOM--.

UNITED STATES PATENT AND TRADEMARK OFFICE
CERTIFICATE OF CORRECTION

PATENT NO. : 5,071,739

DATED : December 10, 1991

INVENTOR(S) : Hidenobu Ohya, et al

It is certified that error appears in the above-indentified patent and that said Letters Patent is hereby corrected as shown below:

Claim 8, column 40, line 55, change "$1 \times 10^{-3}$" to --$1 \times 10^{-2}$--.

Signed and Sealed this

Twenty-ninth Day of June, 1993

Attest:

MICHAEL K. KIRK

Attesting Officer     Acting Commissioner of Patents and Trademarks